United States Patent [19]
Dahl

[11] 4,155,357
[45] May 22, 1979

[54] PATIENT VENTILATOR DISCONNECT ALARM

[75] Inventor: William R. Dahl, Littleton, Colo.

[73] Assignee: Sandoz, Inc., East Hanover, N.J.

[21] Appl. No.: 881,823

[22] Filed: Feb. 27, 1978

Related U.S. Application Data

[63] Continuation of Ser. No. 749,478, Dec. 10, 1976, abandoned.

[51] Int. Cl.$^2$ ............................................. A61M 16/00
[52] U.S. Cl. .................................. 128/145.8; 137/557; 340/605
[58] Field of Search ............... 128/145.5, 145.6, 145.8, 128/142 R, 142.2, 142.3, 142.4, 188, 203, DIG. 17, DIG. 29; 137/557; 340/279, 240, 242

[56] References Cited

U.S. PATENT DOCUMENTS

| | | | |
|---|---|---|---|
| 3,802,417 | 4/1974 | Lang | 128/DIG. 29 |
| 3,870,012 | 3/1975 | Metevier | 128/145.8 X |
| 3,906,934 | 9/1975 | Haverland | 340/279 X |
| 3,910,270 | 10/1975 | Stewart | 128/145.8 |
| 3,916,889 | 11/1975 | Russell | 128/145.8 |
| 3,951,143 | 4/1976 | Kitrilakis et al. | 128/DIG. 17 |
| 4,012,732 | 3/1977 | Herrick | 340/279 |
| 4,067,329 | 1/1978 | Winicki | 128/145.8 |

FOREIGN PATENT DOCUMENTS

1398752  6/1975  United Kingdom ............ 128/DIG. 29

*Primary Examiner*—Henry J. Recla
*Attorney, Agent, or Firm*—Gerald D. Sharkin; Robert S. Honor; Walter F. Jewell

[57] ABSTRACT

Normal breathing cycles of a ventilator cause an alarm controller circuit to emit a periodic pulse which resets a timer circuit thereby maintaining an alarm device in an "off" condition. Patient disconnect is sensed by an alarm trigger circuit which sends an inhibit pulse to the controller circuit inhibiting the timer circuit reset pulse. This causes the timer to "time out" thereby turning on an alarm actuator circuit which causes an audible and/or visual alarm condition.

9 Claims, 3 Drawing Figures

PATIENT VENTILATOR DISCONNECT ALARM

This is a continuation, of application Ser. No. 749,478 filed Dec. 10, 1976 now abandoned.

BACKGROUND OF THE INVENTION

This invention relates to alarm devices. More specificaly it relates to patient disconnect alarms for ventilators.

Prior art patient disconnect alarms for ventilators merely monitored pressure in a ventilator circuit, eg., at the patient manifold, and if the pressure did not exceed a preset pressure limit an alarm would sound after a time delay.

This system has a serious drawback in that any restriction at the end of the patient circuit, eg., a tracheotomy tube, can cause circuit pressure to increase even with the patient disconnected, thus causing the monitor to falsely indicate that the patient is connected. If the pressure drop created by a bacterial filter and/or a humidifier is added to that of a tracheotomy tube it becomes relatively easy for a pressure monitor to falsely indicate that a patient is connected to the ventilator.

Also, if the pressure sensor is connected to the patient manifold, bacteria can enter the sensing tube, thus causing sterility and cross-contamination problems.

SUMMARY OF THE INVENTION

Figure 1:
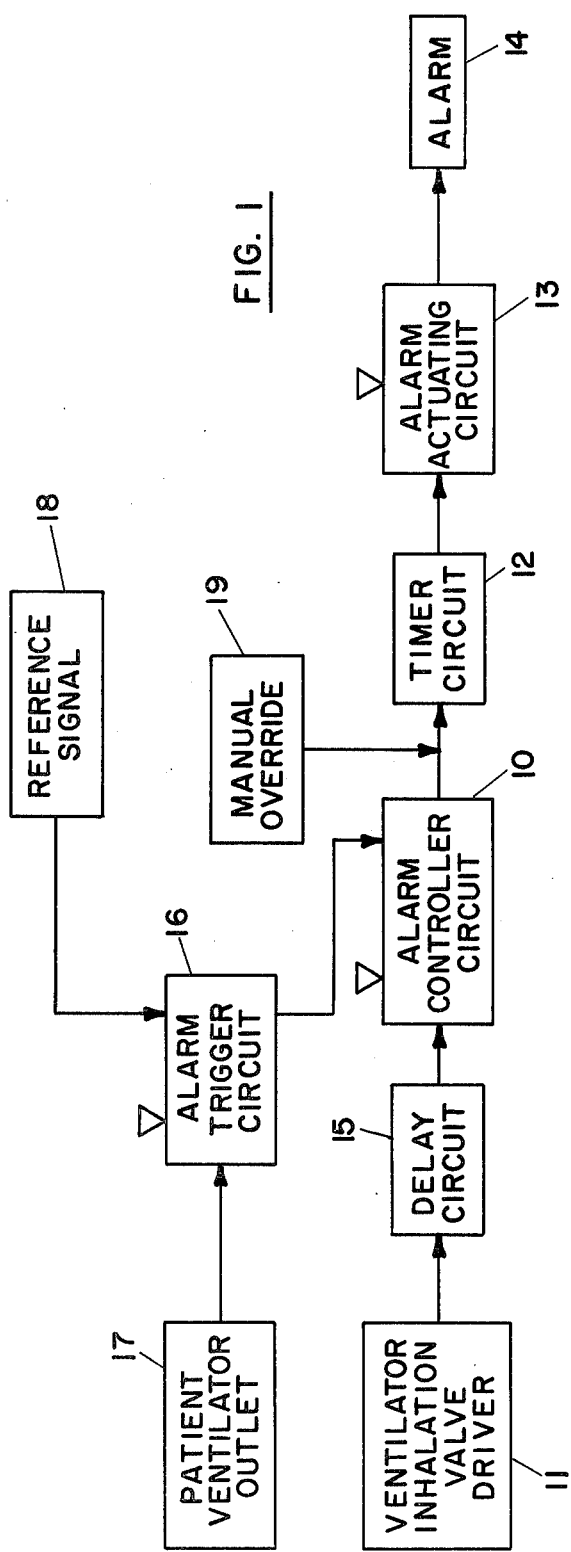
FIG. 1 shows a block diagram of a Patient Ventilation Disconnect Alarm according to the invention.

In accordance with the invention there is provided a fluidic patient disconnect alarm controller apparatus for ventilators utilizing a pressurized source of gas, eg., oxygen, for operating the fluidic circuity. The apparatus comprises a patient disconnect alarm controller circuit having a first input port for sensing a periodic pressure signal from the ventilator, and providing a timer reset signal at a first output port thereof; and a second input port for sensing an alarm trigger circuit inhibit signal from a fluidic alarm trigger circuit and providing an inhibit signal at a second output port thereof.

The fluidic alarm trigger circuit is provided with an input port for sensing the pressure of a breathing gas, eg. oxygen, at the patient outlet of the ventilator, an output port providing an alarm controller inhibit signal in response to a sensed pressure loss in the breathing hose representing a patient disconnect, and means coupling the inhibit signal to the second input port of the alarm controller circuit.

A timer circuit is provided having an input port coupled to the first output port of the alarm controller circuit, and an output port providing a timed output pressure signal.

An alarm actuating circuit is provided having an input port coupled to the output port of the timer circuit and an output port providing an output pressure signal to an alarm means.

The alarm means is coupled to the output port of the alarm actuating circuit.

Preferably the fluidic alarm trigger circuit has at least one input port for receiving a pressure reference signal, corresponding to a predetermined minimum patient breathing hose gas pressure.

More preferably the alarm trigger circuit consists of a six-stage fluidic circuit having three proportional amplifiers connected in series with each other and with three serially connected fluidic flip flops. The trigger circuit provides means for connecting the inputs of one of the fluidic amplifier to a PEEP (positive-end expiratory pressure) signal and the patient breathing hose signal source. Also provided are means for connecting inputs of another one of the fluidic amplifiers to a pressure limit signal source and an adjustable positive-end expiratory pressure signal. The trigger circuit also provides for means connecting the outputs of one of the flip flops to the fluidic alarm controller circuit as a source of the alarm signal and to the atmosphere. The trigger circuit can provide an output in response to a small differential pressure at its inputs.

Preferably the timer circuit comprises a fluidic capacitance, coupled to a variable fluidic resistance in communication with ambient atmosphere for timed discharge of the fluidic charge of the capacitance.

Preferably a gate valve is coupled between the alarm controller circuit and the timer circuit, the gate valve comprising, a diaphragm switch having a sealed chamber provided with first and second ports coupled respectively to the source of the controller circuit timer signal and the timer circuit input port, the diaphragm permitting both communication between the first and second ports and sealing of the first and second ports, the diaphragm actuated for sealing by a third input port coupled to the second output port of the alarm controller circuit.

Preferably the alarm actuating circuit comprises a gate valve comprising a diaphragm switch having a sealed chamber provided with a first and second ports coupled respectively to a source of alarm actuating fluidic pressure source gas and the alarm means, the diaphragm permitting both communication between the first and second ports and sealing of the first and second ports, the diaphragm actuated for sealing by a third input port coupled to the source of the timed output pressure signal of the timer circuit.

Preferably a pressure regulator circuit is coupled upstream of the fluidic capacitance, the pressure regulator circuit comprising, a diaphragm switch having a sealed chamber provided with a first port in fluidic communication with the fluidic capacitance of the timer circuit and a second port in fluidic communication with ambient atmosphere, the diaphragm permitting both communication between the first and second ports and sealing of the first and second ports, the diaphragm actuated for sealing by a third input port coupled to a variable fluidic pressure source. It is the purpose of the regulator to provide a relatively constant time delay period, regardless of patient breathing rates.

Preferably the periodic pressure signal to the first input port of the alarm controller circuit from the ventilator apparatus is transmitted by a signal delay circuit which comprises a diaphragm switch having a sealed chamber provided with a first port in fluidic communication with the ventilator inspiratory valve controlling means and a second port coupled to the first input port of the alarm controller circuit, the diaphragm permitting both communication between the first and second ports and sealing of the first and second ports, the diaphragm actuated for sealing by a third input port in fluidic communication with ventilator expiratory valve controlling means.

The invention also provides a manually operable pressure switch (e.g. manual override) fluidically connected to the first input port of the gate valve coupled between the alarm controller circuit and the timer circuit, the pressure switch allowing fluidic pressure to override the diaphragm when the diaphragm is actuated closed by the alarm controller circuit inhibit signal.

Broadly in the operation of the Patient Ventilator Disconnect Alarm of this invention, (See FIG. 1) the fluidic alarm controller circuit 10 senses a periodic pressure signal from the ventilator apparatus inhalation valve driver 11 and in the absence of an inhibiting signal provides a timer reset signal. This timer reset signal fluidically charges a capacitance in the timer circuit 12 which maintains a pressure signal on the alarm actuating circuit 13 preventing it from actuating the alarm means 14. A variable resistance in the timer circuit 12 allows for a predetermined timed discharge e.g., 15 to 30 seconds, of the fluidic charge of the capacitance which in the absence of a timer reset pressure signal, allows the timer to "time out", e.g., discharge its fluidic charge.

When the timer circuit 12 pressure signal drops below that maintained at the alarm actuating circuit 13, the circuit 13 is activated causing the alarm means 14 to indicate a patient disconnect. The alarm may be an audible and/or visual signal.

The timer inhibit signal is provided by the fluidic alarm trigger circuit 16 which senses the pressure of the oxygen at the patient outlet of this ventilator 17 and compares it with a reference signal 18. An alarm trigger signal e.g., a timer reset inhibiting signal, is sent in response to a sensed pressure loss in the breathing hose representing that the patient is disconnected. The reference signal 18 also compensates for the use of PEEP which would otherwise negate the use of the alarm.

Upon correction of the disconnect condition, the alarm maybe reset by means of a manual override 19 of the timer inhibit signal.

Figure 2:
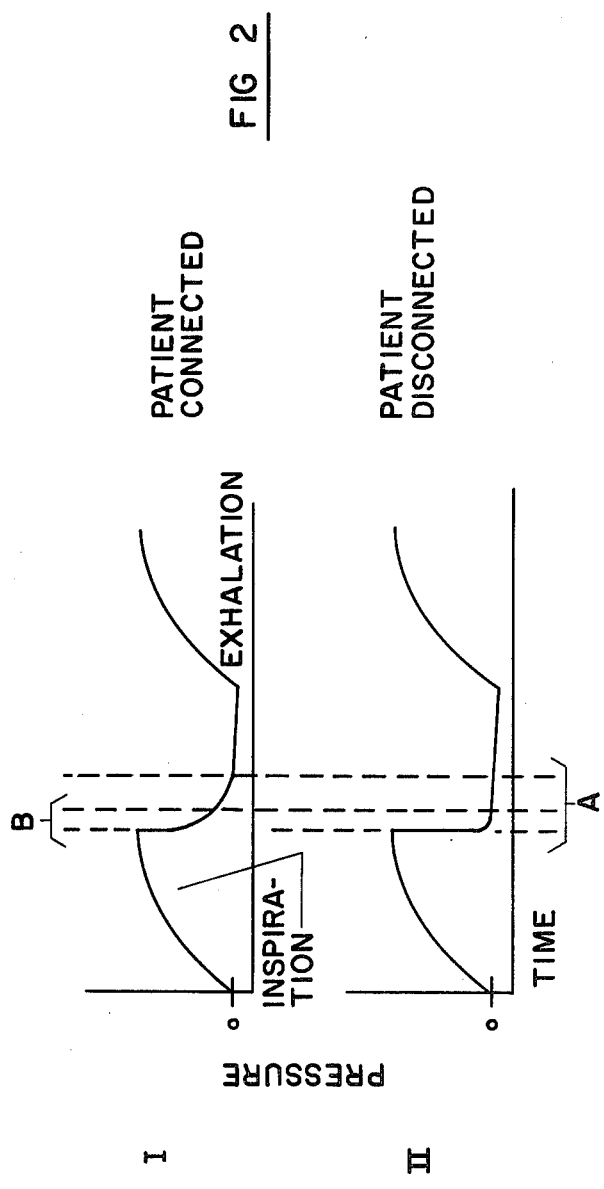
FIG. 2 is a diagram showing the change in the ventilator patient circuit pressure with respect to time during a breathing cycle when a patient is both connected to a ventilator, and disconnected from a ventilator.

As shown in FIG. 2 the pressure in the patient circuit is monitored during the time interval shown at A in diagrams I and II. This interval represents the oxygen pressure decay time between the ending of the inspiration period and the beginning of the exhalation period.

When the patient is connected to the ventilator the oxygen pressure decay period A is gradual, as contrasted with the sharp decay shown when the patient is disconnected from the ventilator. Typically, if the oxygen pressure signal exceeds 4-5 cm. $H_2O$ during the monitoring period (A), no timer inhibit signal will be sent by the fluidic alarm trigger circuit.

The signal delay circuit 15 serves to delay the beginning of the monitoring of the time interval A slightly (interval B FIG. 2). Otherwise, compliant items in the patient circuit such as humidifiers mock the appearance of a patient.

An advantage of the apparatus of this invention is that by sensing patient pressure at the ventilator outlet, upstream of a bacterial filter and humidifier, the sensing means e.g., tube is in the clean port of the circuit, and sanitation is not a problem.

DETAILED DESCRIPTION OF AN EMBODIMENT OF THE INVENTION

Figure 3:
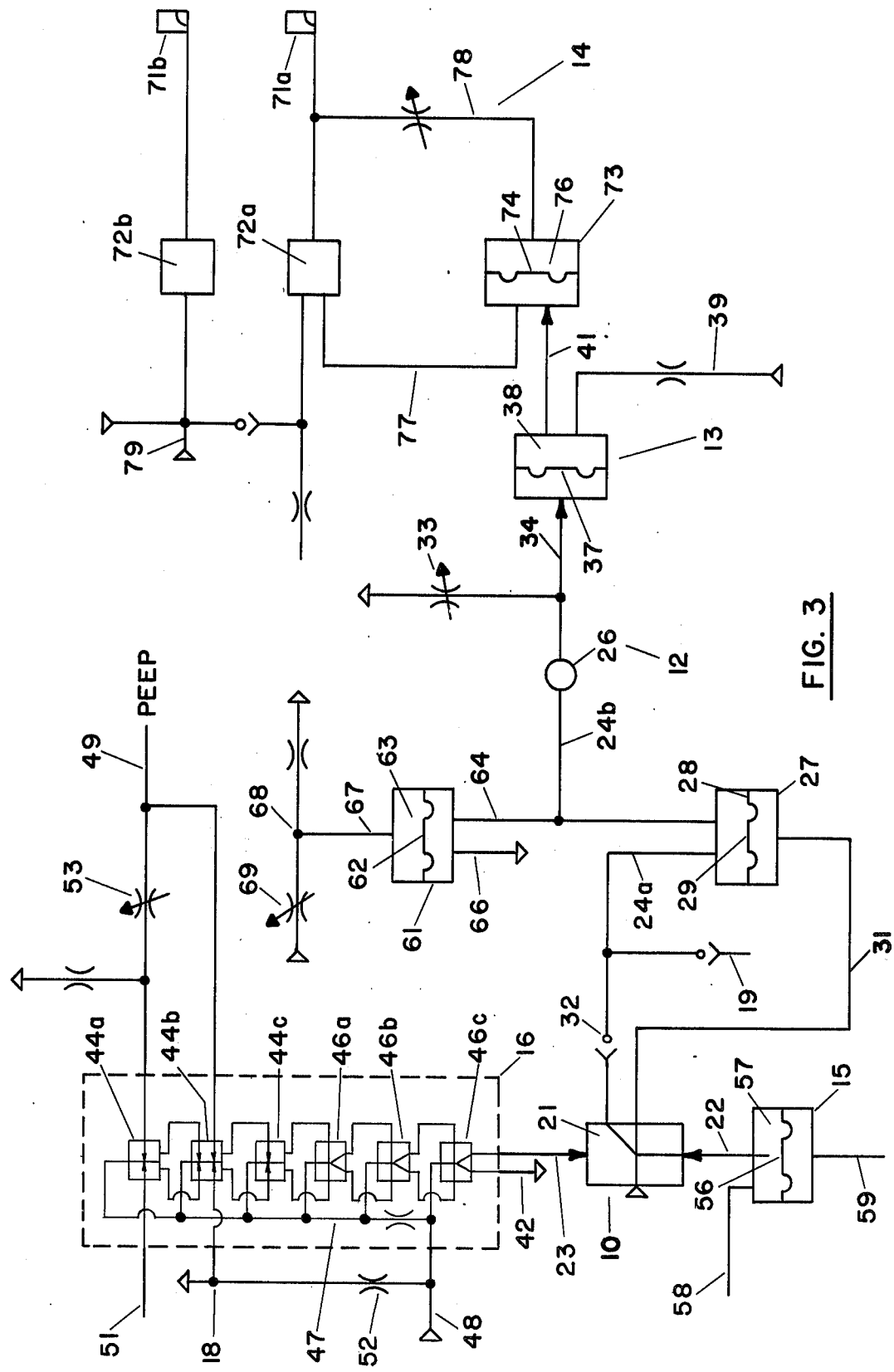
FIG. 3 is a schematic view of the fluidic circuity illustrated in FIG. 1.

An embodiment of the invention is depicted in FIG. 3 wherein the alarm controller circuit 10 comprises an Inhibited OR gate 21, having a ventilator signal input 22 and an alarm signal input 23. Fluidic conduits 24a and 24b connect a timer circuit reset output signal to the timer circuit 12 fluidic capacitance 26 via a gate valve 27.

The gate valve 27 comprises a diaphragm switch 28 having a sealed chamber 29, which provides fluidic communication between the conduit parts 24a and 24b. Diaphragm 28 is actuated for sealing of conduit parts 24a and 24b by the "normally on" signal output 31 of the Inhibited OR gate 21. A one way valve 32 is provided to prevent fluidic back flow from a manual override 19.

An adjustable orifice, e.g., variable resistance 33 allows for the timed discharge of the fluidic charge of the capacitance 26 to the atmosphere. The capacitance 26 maintains a timed output pressure signal 34 at the alarm actuating circuit 13 preventing actuation of the alarm means shown generally at 14. The alarm actuating circuit 13 comprises a gate valve having a diaphragm switch 37 and a sealed chamber 38, which provides fluidic communication between a regulated oxygen signal (alarm actuating fluidic pressure source) 39 and an alarm means actuating signal 41. Diaphragm 37 is actuated for sealing conduits 39 and 41 by the timer circuit output pressure signal 34.

The alarm signal input 23 to the Inhibited OR 21 is provided by the fluidic alarm trigger circuit 16. The preferred form of circuit 16 is shown as comprising a six-stage fluidic device incorporating three proportional amplifiers 44a, 44b, and 44c, connected in series with each other and in series with three serially connected flip flops 46a, 46b, and 46c. Each of the six circuits has its supply input coupled along the conduit 47 to the regulated oxygen signal 48. Also each of circuits 44a, 44b, 44c, 46a, 46b and 46 c have their control inputs coupled to the respective outputs of the preceding stage. The control inputs of the first proportional amplifier 44a are coupled respectively to the output of a PEEP circuit 49 and a patient reference line (patient manifold) 51.

An additional input to the alarm trigger circuit 16 includes a regulated oxygen signal 18 coupled with the Orifice 52 to supply a reference oxygen signal to proportional amplifier 44b. Reference 44b is additionally supplied with a regulated signal from the PEEP circuit 49 via adjustable orifice 53.

The ventilator signal input 22 to the Inhibited OR 21 is preferably supplied via a signal delay circuit 15. The circuit 15 comprises a diaphragm switch 56 having a sealed chamber 57, which provides fluidic communication between the inspiratory side of the ventilator OR/NOR circuit signal 58 e.g., ventilator inspiratory valve controlling means, and input signal 22 to the Inhibited OR 21. Diaphragm 56 is actuated for sealing of fluidic OR/NOR expiratory signal 58 and the input signal 22 by the expiratory side of the Ventilator OR/NOR circuit signal, 59 e.g., ventilator inspiratory valve controlling means. The switching delay characteristics of circuit 15 is sufficient to delay the monitoring time interval A, for a period B (see FIG. 2).

In a preferred embodiment of the invention a pressure regulator circuit 61 is fluidically coupled upstream of the fluidic capacitance 26. The pressure regulator circuit 61 comprises a diaphragm switch 62 having a sealed chamber 63, which provides a fluidic communication between the fluidic capacitance 26 via conduit 64 and the atmosphere via conduit 66. Diaphragm 62 is actuated for sealing of conduits 64 and 66 by port 67 which is coupled to a variable fluidic pressure source 68, e.g., oxygen.

The alarm means shown generally at 14 is depicted as an audible alarm, though it is understood that a combination visual and audible alarm is within the scope of this invention. It is also understood that single or multiple alarms may be used.

The alarm means 14 comprises a pair of audible whistles 71a and 71b which are activated by a pair of conventional alarm drivers 72a and 72b. It is a feature of the alarm means 14 that an oscillator valve may be incorporated to create an intermittant alarm. One such oscillator valve is shown at 73. It comprises a diaphragm switch 74 having a sealed chamber 76, which provides fluidic communication between the alarm means actuating signal 41 and the alarm driver 72a and 72b actuating signal 77. Diaphragm 74 is actuated for sealing signals 41 and 77 by an oxygen flow interuptor signal 78.
Diaphragm amplifiers #128, Fred Knapp Engineering Co., Racine, Wisc.

A provision of alarm 71b and driver 72b is that they may be actuated as an alarm for other function of the ventilator by means of ventilator signal 79.

When the reason for a patient disconnect has been corrected, the alarm may be reset, e.g., the capacitance 26 fluidically changed, by means of the manual override 19. This override generates sufficient pressure to overcome the inhibit signal output 31 and allow fluidic communication within chamber 29. fluidic communication between the OR/NOR exspiratory signal 58 and input 22 of the Inhibited OR gate 21. The diaphragm switch 56 causes a 40 millisecond delay approximately in the input signal 22 and in the absence of an inhibit signal input 23, a timer reset pulse is sent out via 24a and 24b to charge the fluidic capacitance 26. The fluidic charge in the capacitance 26 maintains an output pressure signal 34 on the alarm actuating circuit 13. Signal 34 has a preset time period set by the variable resistance 33 as it discharges the fluidic charge of the capacitance 26 to the atmospheric. If at the end of the time period the capacitance 26 has not been recharged, the capacitance 26 "times out" and the output pressure signal 34 ceases, causing the actuation of circuit 13. Recharging capacitance 26 before it "times out" maintains output signal 34, inhibiting the alarm circuit 13.

The maximum pressure in the capacitance 26 is limited to 20-30 cm H2O by the pressure regulator circuit 61. This makes the capacitance 26 discharge less dependent upon the cycling rate of the ventilator. The reference pressure of 20-30 cm H2O is provided by the variable fluidic pressure source 68 by adjustment of the variable resistance 69.

An alarm signal input 23 to the Inhibited OR gate 21 from the alarm trigger circuit 16 inhibits the timer circuit reset output signal to the capacitance 26 causing the capacitance 26 to "time out" thus causing the alarm means 70 to be actuated.

The alarm trigger circuit 16 monitors a patient circuit input 51 and compares it with a regulated oxygen reference signal 48 and a PEEP signal 49. The restricted orifice 52 sets the swithcing level of circuit 16 at about 4 to 6 cm H2O. A patient circuit input 51 greater than 8 cm H2O prevents an alarm signal and the fluidic charge is vented to atmosphere at 42.

A patient circuit input 51 less than 4 to 6 cm H2O switches the signal from vent 42 to an alarm signal input 23 to the Inhibited OR gate 21. An inhibit signal output 31 from gate 21, seals the chamber 29 causing the capacitance 26 to "time out" and hence cause the alarm means 14 to be actuated.

What is claimed is:

1. A fluidic patient disconnect alarm system for a fluidically controlled patent ventilator apparatus comprising control means utilizing a pressurized breathing gas for intermittently supplying gas to a patient breathing hose communicating with an expiratory valve which comprises;

first means responsive to said ventilator apparatus for providing a periodic inspiratory fluidic pressure signal;

patient breathing hose disconnect alarm trigger circuit means for producing a fluidic pressure signal representing a patient disconnect;

a fluidic alarm controller circuit having first and second input ports and first and second output ports, the first input port coupled to said first means, said controller circuit including means responsive to said periodic inspiratory fluidic pressure signal from the ventilator for producing an output timer reset signal at the first output port; the second input port coupled to said patient breathing hose disconnect alarm trigger circuit means, said controller circuit including means responsive to said fluidic pressure signal from a patent breathing hose disconnect alarm trigger circuit means for producing a timer reset inhibit signal at the second output port;

timer circuit means; an alarm actuating circuit; alarm means;

said alarm trigger circuit means having an input port for sensing the pressure of the breathing gas at the patient hose outlet, an output port in fluidic communication with the input port and providing said fluidic pressure signal to the second input port of the alarm controller circuit in response to a sensed pressure loss in the breathing hose representing a patient disconnect;

said timer circuit means having an input port fluidically coupled to the first output port of the alarm controller circuit for receiving said reset signal, and an output port coupled to said alarm actuating circuit and providing a timed output pressure signal said alarm actuating circuit having an input port fluidically coupled to the output port of the timer circuit means, and an output port for providing an alarm actuating pressure signal and fluidically coupled to actuate said alarm means;

said alarm actuating circuit having means for providing said alarm actuating pressure signal to said alarm means in the absence of said timed output pressure signal from said timer circuit means.

2. The apparatus according to claim 1 wherein the fluidic alarm trigger circuit means has at least one additional input port for receiving a pressure reference signal, corresponding to a predetermined minimum patient breathing hose gas pressure and means for producing a fluidic pressure signal corresponding to said predetermined minimum patient breathing hose gas pressure.

3. The apparatus according to claim 2 wherein the timer circuit means input and output ports are coupled to a fluidic capacitance, which capacitance is additionally coupled to a variable fluidic resistance in communication with ambient atmosphere providing for the timed discharge of a fluidic charge of the capacitance.

4. The apparatus according to claim 3 wherein a gate valve is coupled between the alarm controller circuit and the timer circuit, the gate valve comprising;
   a diaphragm switch having a sealed chamber provided with first and second ports coupled respectively to the first output port of the alarm controller circuit and the timer circuit input port, the diaphragm permitting both communication between the first and second ports and sealing of the first and second ports, the diaphragm actuated for sealing by a third input port coupled to the second output port of the alarm controller circuit.

5. The apparatus according to claim 4 wherein the alarm actuating circuit comprises a gate valve comprising a diaphragm switch having a sealed chamber provided with first and second ports coupled respectively to the output port of the fluidic capacitance and the alarm means, the diaphragm permitting both communication between the first and second ports and sealing of the first and second ports, the diaphragm actuated for sealing by a third input port coupled to the output of the timer circuit means.

6. The apparatus according to claim 5 wherein a pressure regulator circuit is coupled upstream of the fluidic capacitance, the pressure regulator circuit comprising, a diaphragm switch having a sealed chamber provided with a first port in fluidic communication with the fluidic capacitance of the timer circuit and a second port in fluidic communication with atmosphere, the diaghragm permitting both communication between the first and second ports and sealing of the first and second ports, the diaphragm actuated for sealing by a third input port coupled to a variable fluidic pressure source.

7. The apparatus according to claim 6 wherein the first means providing said periodic pressure signal to the first input port of the alarm controller circuit from the ventillator apparatus is transmitted by a signal delay circuit which comprises a diaphragm switch having a sealed chamber provided with a first port in fluidic communication with the ventilator inspiratory valve controlling means and a second port coupled to the first input port of the alarm controller circuit, the diaphragm permitting both communication between the first and second ports and sealing of the first and second ports, the diaphragm actuated for sealing by a third input port in fluidic communication with ventilator expiratory valve controlling means.

8. The apparatus according to claim 7 further comprising a manually operable pressure switch fluidically connected to the first input port of the gate valve coupled between the alarm controller circuit and the timer circuit, the pressure switch allowing fluidic pressure to override the diaphragm when the diaphragm is actuated closed by the alarm controller circuit inhibit signal.

9. The apparatus according to claim 2 wherein the alarm trigger circuit comprises three fluidic proportional amplifiers connected in series, and three fluidic flip flops connected in series with each other and in series with an output of the three fluidic amplifiers, and wherein the alarm trigger circuit further comprises means for connecting the inputs of one of the fluidic amplifier to a positive end-expiratory pressure signal and patient breathing hose signal source, and for connecting inputs of another one of the fluidic amplifiers to a pressure limit signal source and an adjustable positive end-expiratory pressure signal, and wherein the alarm trigger circuit further comprises means connecting the outputs of one of the flip flops to the fluidic alarm controller circuit as a source of the alarm signal and to the atmosphere.

* * * * *